United States Patent [19]

Quijano et al.

[11] Patent Number: 5,609,626
[45] Date of Patent: Mar. 11, 1997

[54] STENT DEVICES AND SUPPORT/RESTRICTOR ASSEMBLIES FOR USE IN CONJUNCTION WITH PROSTHETIC VASCULAR GRAFTS

[75] Inventors: R. C. Quijano, Laguna Hills; Aws Nashef, Huntington Beach, both of Calif.

[73] Assignee: Baxter International Inc., Deerfield, Ill.

[21] Appl. No.: 264,225

[22] Filed: Jun. 22, 1994

Related U.S. Application Data

[63] Continuation of Ser. No. 871,414, Apr. 21, 1992, abandoned, which is a continuation-in-part of Ser. No. 500,821, Mar. 28, 1990, abandoned, which is a continuation-in-part of Ser. No. 359,449, May 31, 1989, abandoned.

[51] Int. Cl.$^6$ ............................................. A61F 2/06
[52] U.S. Cl. ............................ 623/1; 623/12; 606/153
[58] Field of Search ................................ 623/1, 11, 12; 606/153, 198

[56] References Cited

U.S. PATENT DOCUMENTS

| | | |
|---|---|---|
| 2,127,903 | 8/1938 | Bowen . |
| 2,453,056 | 11/1948 | Zack . |
| 3,254,650 | 6/1956 | Collito . |
| 3,254,651 | 6/1956 | Collito . |
| 3,974,526 | 8/1976 | Dardik et al. . |
| 3,988,782 | 11/1976 | Dardik et al. . |
| 4,056,854 | 11/1977 | Boretos et al. . |
| 4,086,665 | 5/1978 | Poirier . |
| 4,247,292 | 1/1981 | Angell . |
| 4,340,977 | 7/1982 | Brownlee et al. . |
| 4,350,492 | 9/1982 | Wright et al. . |
| 4,352,358 | 10/1982 | Angelchik . |
| 4,728,328 | 3/1988 | Hughes et al. ........................ 623/12 |
| 4,804,382 | 2/1989 | Turina et al. ......................... 623/1 |
| 4,816,029 | 3/1989 | Penny, III et al. ................... 623/2 |
| 4,851,000 | 7/1989 | Gupta ..................................... 623/2 |
| 4,938,740 | 7/1990 | Melbin .................................. 600/36 |
| 4,957,508 | 9/1990 | Kaneko et al. ...................... 623/12 |
| 5,059,211 | 10/1991 | Stack et al. ........................ 606/198 |
| 5,078,735 | 1/1992 | Mobin-Uddin ....................... 623/1 |
| 5,089,014 | 2/1992 | Holfert . |
| 5,108,430 | 4/1992 | Ravo ................................. 623/11 X |
| 5,193,289 | 3/1993 | Jensen .............................. 623/12 X |
| 5,236,447 | 8/1993 | Kubo et al. ........................... 623/1 |
| 5,399,352 | 3/1995 | Hanson ............................... 424/423 |

FOREIGN PATENT DOCUMENTS

| | | | |
|---|---|---|---|
| 0202031 | 11/1986 | European Pat. Off. ............. 623/12 |
| 303767 | 2/1989 | European Pat. Off. . |
| 2657255 | 12/1976 | Germany . |
| WO81/00668 | 3/1981 | WIPO . |
| WO82/01644 | 5/1982 | WIPO . |
| WO87/04915 | 8/1987 | WIPO . |
| WO89/02254 | 3/1989 | WIPO . |
| WO80/01460 | 7/1989 | WIPO . |
| 9014804 | 12/1990 | WIPO ................................... 623/1 |
| 9300868 | 1/1993 | WIPO ................................... 623/1 |

*Primary Examiner*—Michael J. Milano
*Attorney, Agent, or Firm*—Raymond Sun

[57] ABSTRACT

Exovascular and endovascular stent devices and associated support/restrictor assemblies for use in conjunction with prosthetic vascular grafts, including venous valve grafts made from preserved bioprosthetic venous valves. Also disclosed are methods for preparing vascular grafts such as venous valve grafts using the devices and assemblies of the present invention.

8 Claims, 5 Drawing Sheets

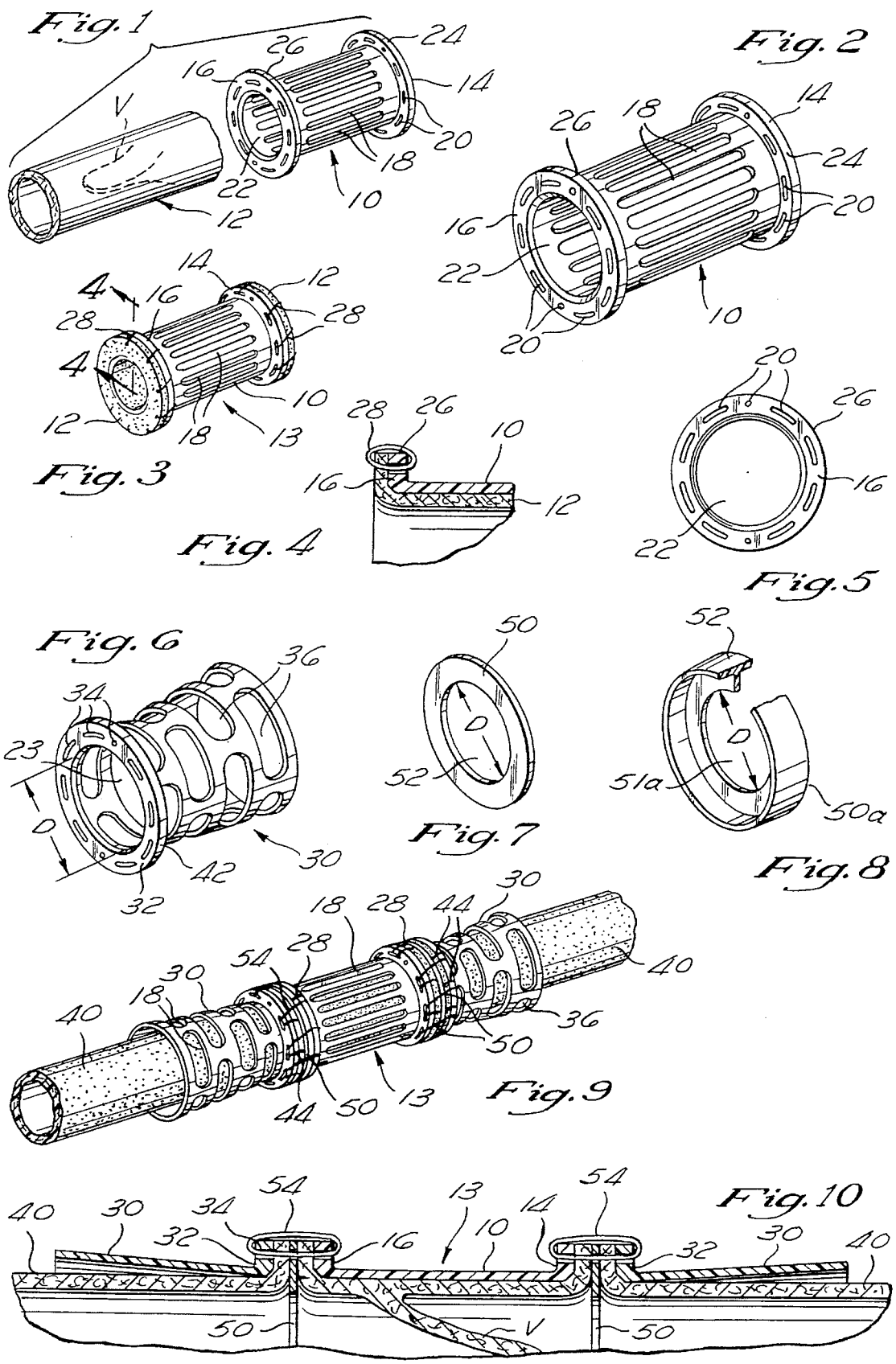

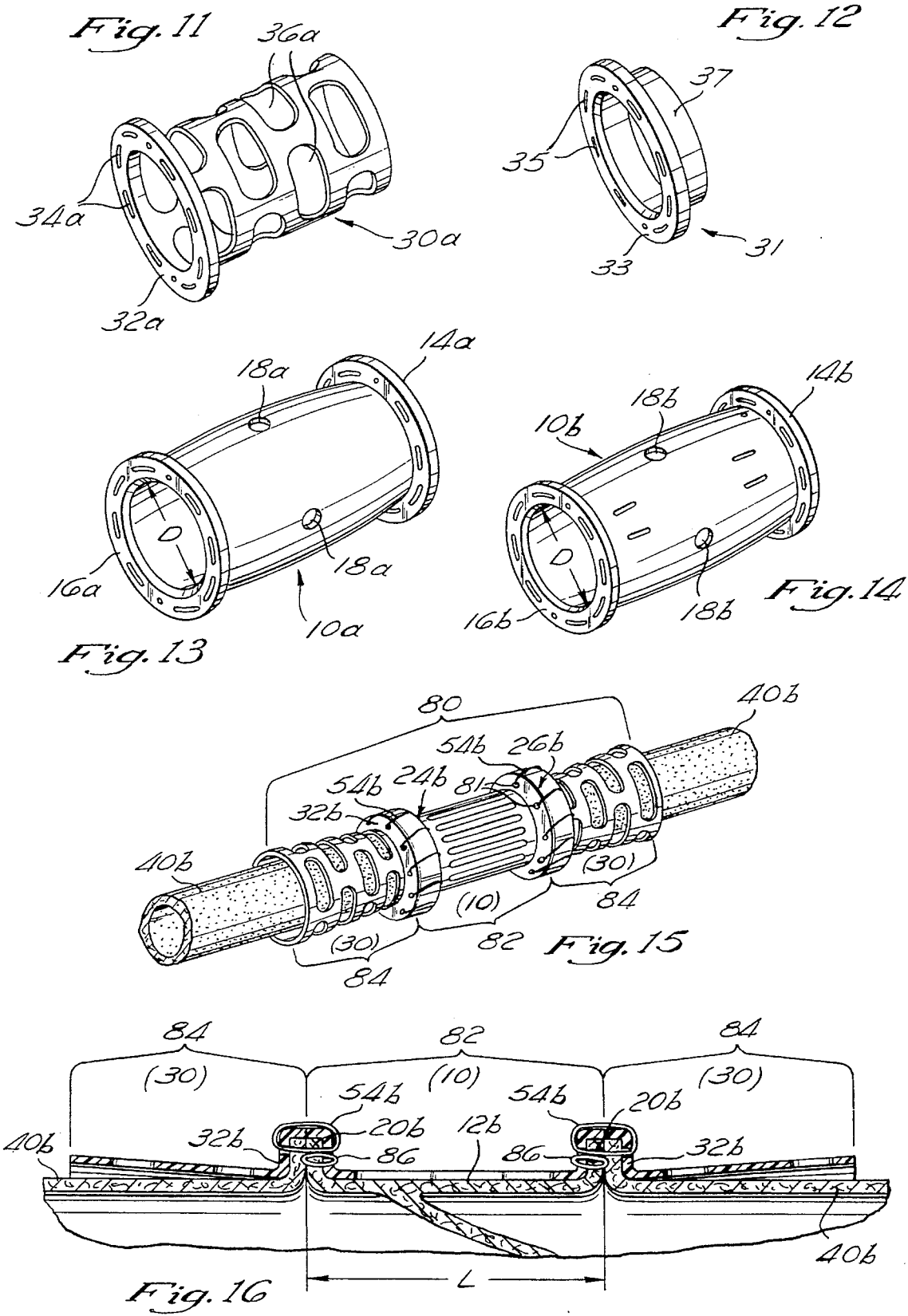

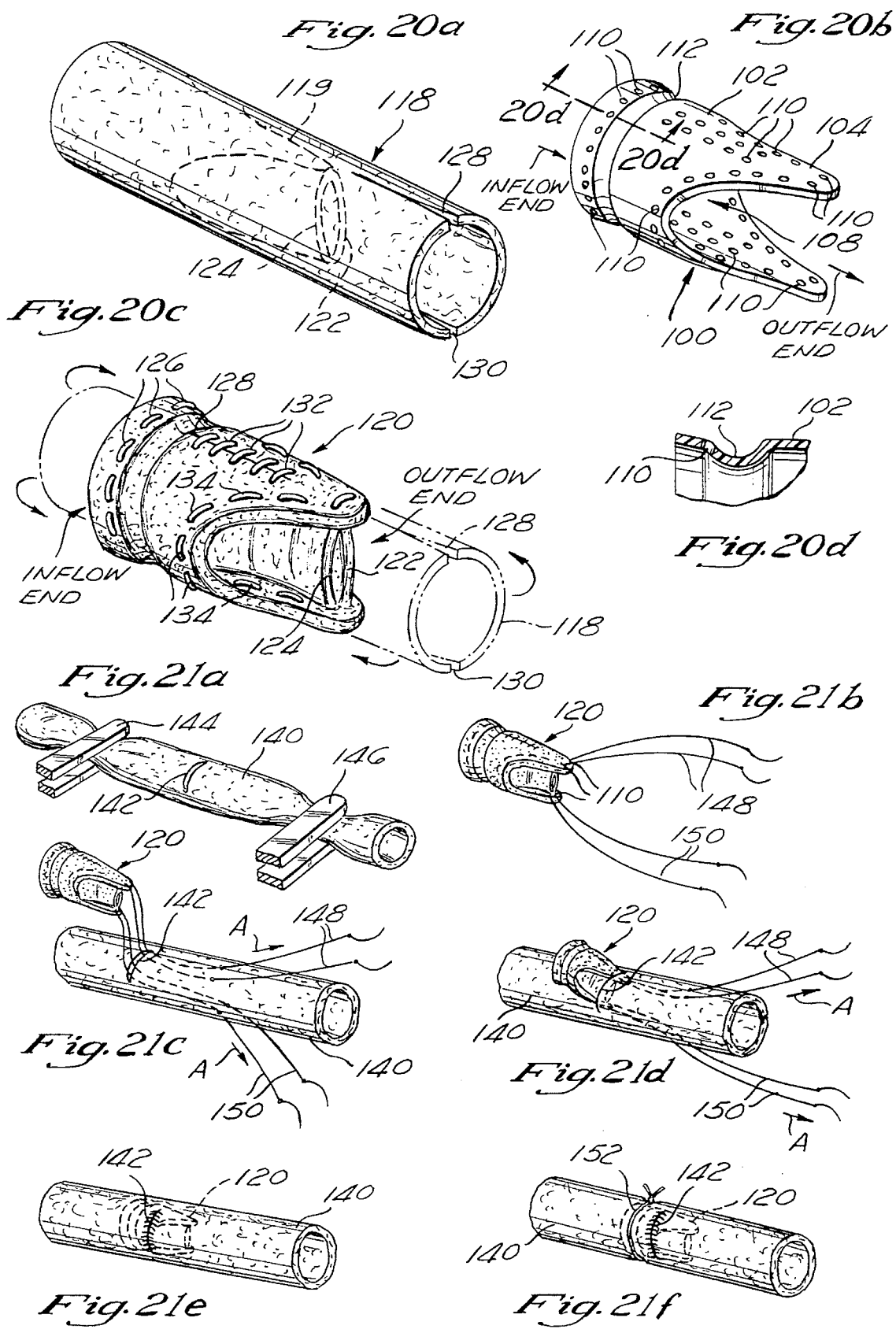

STENT DEVICES AND SUPPORT/RESTRICTOR ASSEMBLIES FOR USE IN CONJUNCTION WITH PROSTHETIC VASCULAR GRAFTS

RELATED APPLICATIONS

This is a continuation of U.S. patent application Ser. No. 07/871,414, filed Apr. 21, 1992, now abandoned, which is a continuation-in-part of U.S. patent application Ser. No. 07/500,821, filed Mar. 28, 1990, now abandoned, which is a continuation-in-part of U.S. patent application Ser. No. 07/359,449, filed May 31, 1989, now abandoned.

FIELD OF THE INVENTION

The present invention relates generally to bioprosthetic vascular implants and, more particularly, to stents and support/guide assemblies which are operative to (a) provide support for, (b) facilitate the implantation of, and (c) minimize thromboembolic complications resulting from artificial or bioprosthetic vascular implants.

BACKGROUND OF THE INVENTION i. Prosthetic Vascular Grafts Including Venous Valvular Implants

Modern vascular surgical procedures often involve the grafting of a tubular prosthetic implant of artificial or natural origin into an existing blood vessel for the purpose of replacing or bypassing a segment of diseased or damaged blood vessel. Many such procedures are accomplished by surgically removing the diseased or damaged segment of blood vessel, and subsequently replacing the removed segment of vessel with an appropriately sized tubular implant graft. The implant graft is typically held in place by anastomosing the ends of the implant graft to the opposing ends of the resected blood vessel.

In individuals who suffer from chronic venous valvular insufficiency, vascular grafting procedure have utilized to transplant functioning venous valves into the affected veins of the lower extremities. The transplantation of functioning venous valves in such individuals is therapeutically important as chronic incompetence or absence of venous valves into the veins of the lower extremities is known to give rise to numerous pathological consequences. For example, incompetence or absence of venous valves at the saphenofemoral or saphenopopliteal junctions may result in noncosmetic varices of the primary and/or secondary veins of the lower leg and ankle. Additionally, deep venous hypertension of the lower limb may occur. Such venous hypertension may result in lymphedema, aberrant pigmentation of the skin and, in severe cases, the formation of necrotizing lesions known as "venous ulcers".

Surgical transplantation of one or more functioning venous valves into a valve-deficient vein is a viable means of restoring venous valvular function to the valve deficient vein. The routine use of venous valve "transplant" procedures has heretofore been largely limited to autograft procedures. Such autograft procedures require the initial surgical excision of an autologous segment of viable vein (i.e. vein having a functioning venous valve therein) from one site within the patient's body, followed by subsequent transplantation of the harvested autograft to other veins wherein the venous valvular insufficiency has occurred. Such autograft transplant procedures are problematic because of (a) difficulties encountered in locating suitable segments of vein having viable venous valves therein and/or (b) the necessity of forming a separate incision or second surgery to harvest the venous valve autograft and/or (c) size mismatching of the harvested venous valve autograft relative to the implant site as may result in subsequent thromboembolic complications and failure of the implanted valve.

In view of the limitations and shortcomings of autograft venous valve transplantation procedures, it is desirable to develop artificial and/or preserved venous valve implants from cadaverous human or animal sources for subsequent transplantation into a human patient. The availability of artificial or bioprosthetic venous valve implants would eliminate the need for second-incision harvesting of homograft tissue and would enable the surgeon to select from an available range of graft sizes to obtain a graft which is specifically size-matched to the diameter of the resected blood vessel.

ii. Presently Known Methods of Preparing Bioprosthetic Grafts

Various chemical tanning or "fixing" procedures have been used to preserve and prevent the breakdown of collagenous tissue grafts. Such "fixing" procedures generally involve the bathing or immersion of the collagenous graft tissue in a collagen cross-linking reagent. Examples of methods for preparing chemically cross-linked collagen or graft materials are found in U.S. Pat. No. 2,900,644 (Rosenberg, et al.), U.S. Pat. No. 3,927,422 (Sawyer), U.S. Pat. No. 3,966,401 (Hancock, et al.), U.S. Pat. No. 3,974,526 (Dardik, et al.), U.S. Pat. No. 4,239,492 (Holman, et al.) and U.S. Pat. No. 4,553,974 (Dewanjee).

Chemically fixed bioprosthetic heart valves and vascular grafts are commercially available. Examples of prosthetic heart valves constructed, at least in part, from chemically fixed biological tissue are described in U.S. Pat. Nos. 4,372,734 (Lane) and U.S. Pat. No. 4,443,895 (Lane). Examples of bioprosthetic vascular grafts prepared from segments of mammalian blood vessel are found in U.S. Pat. Nos. 4,671,797 (Varandecic) and U.S. Pat. No. 4,466,139 (Ketharanathan, et al.).

iii. The Use of Stents to Support Bioprosthetic Tissue

Various rigid stent devices have heretofore been utilized to hold and support bioprosthetic implants, such as heart valves. Examples of stent devices for bioprosthetic heart valves are described in U.S. Pat. Nos. 4,816,029 (Penny, III, et al.) and 4,851,000 (Gupta).

iv. Thromboembolic Complications Known to Result from Turbulent Blood Flow Through Vascular Grafts In the prior art, it has become recognized that abrupt variations in the lumenal diameter of a blood vessel, as may result from improper size matching of a vascular implant graft, may result in thromboembolic complications due to the resultant non-laminar or turbulent flow brought about the abrupt variation in lumenal diameter.

In particular, accurate size matching of vein grafts is difficult because certain peripheral veins normally undergo large amounts of dilation in performance of their normal physiological capacitance function. Thus, even if a vein graft is properly size matched at the time of the surgical implantation, subsequent dilation of the endogenous vein at a location to the non-dilating vein graft may give rise to abrupt variations in lumenal diameter of the blood vessel.

Accordingly, there remains a need in the art for improved vascular implant graft devices and techniques aimed at maximizing the biocompatibility and ease of use of such vascular implant grafts, while minimizing the potential for graft failure or other complications, such as immunoreactions to the implant graft material and/or thromboembolic complications resulting from turbulent blood flow through the implant graft.

SUMMARY OF THE INVENTION

The present invention overcomes some or all of the shortcomings of the prior art by providing an exovascular stent device and dilation restrictor members, useable in connection with said exovascular stent device, for facilitating implantation and functioning of tubular implant grafts such as vascular grafts and venous grafts having functioning venous valves therein.

Additionally, there is provided an endovascular stent device which operates to hold and support a bioprosthetic venous valve for implantation within the lumen of an existing blood vessel.

Further and in accordance with the invention there are provided systems and methods of use, incorporating and utilizing the above-stated exovascular stent, dilation restrictor member(s) and endovascular stent devices.

The exovascular stent device of the invention comprises an elongate tubular body having a hollow bore extending therethrough and flanges formed on either end thereof. A preserved segment of blood vessel is positionable coaxially within the lumen of the exovascular stent device and the ends of such segment of blood vessel are outturned and attached to the outboard surfaces of said end flanges, thereby forming a vascular implant prosthesis.

The dilation restrictor member(s) of the invention comprise an apparatus having an elongate tubular body with a hollow bore extending longitudinally therethrough and a flange formed about one end of said tubular body. The tubular body is passable over the transected end of a blood vessel such that the transected end of said blood vessel. emerges out of the flange end of said tubular body whereby it may be outturned and affixed to the outboard surface of said flange. When so affixed to said blood vessel, the tubular body of the apparatus remains around the outer surface of the blood vessel, thereby functioning to restrict dilation of the blood vessel in the region of said tubular body.

A system or assembly of the present invention comprises the above described a) exovascular stent device and b) dilation restrictor member(s) in conjunction with one another. Optional spacer rings or washers may be interposed therebetween to prevent tissue to tissue contact between the excised end of the endogenous blood vessel and the adjacent end of the implant graft.

An endovascular stent device of the present invention comprises a rigid annular body having a hollow bore extending therethrough and first and second support struts extending longitudinally from one end thereof. Said support struts are configured and positioned to provide supportive attachment for the lateral edges of a blood vessel graft wherein a functioning venous valve is positioned. Accordingly, such endovascular stent device may be utilized as a rigid support device for the formation of a bioprosthetic venous valve implant which is insertable into the lumen of an existing vein. An annular ridge or other attachment means is formed on the outer surface of the endovascular stent to permit an externally applied ligature or other attachment means to hold the endovascular stent (and the accompanying venous valve implant, in position within the lumen of the blood vessel).

Further and more specific aspects of the invention will become apparent to those skilled in the art upon reading and understanding of the following detailed description and the accompanying drawings.

BRIEF DESCRIPTION OF THE DRAWINGS

FIG. 1 is a perspective view of an embodiment of an exovascular stent device of the present invention positioned next to a bioprosthetic vein graft segment which has a venous valve located therein.

FIG. 2 is a perspective view of a first embodiment of an exovascular stent device of the present invention.

FIG. 3 is a perspective view of the first embodiment of the exovascular stent device of the present invention having a bioprosthetic vein graft operatively positioned therein.

FIG. 4 is a longitudinal sectional view through line 4—4 of FIG. 3.

FIG. 5 is an end elevational view of the exovascular stent device shown in FIG. 2.

FIG. 6 is a perspective view of a tapered ring-support member usable in conjunction with the exovascular stent device of the present invention.

FIG. 7 is a perspective view of a gasket member usable in conjunction with the exovascular stent device and tapered ring-support device of the present invention.

FIG. 8 is a perspective view of an alternative gasket member usable in conjunction with the exovascular stent device and tapered ring-support member of the present invention.

FIG. 9 is a perspective view of a vascular implant system of the present invention comprising (a) an exovascular stent device; (b) two (2) dilation restrictor members and (c) two (2) gaskets, said system being shown in an in situ, operative position on a blood vessel.

FIG. 10 is a longitudinal sectional view through line 10—10 of FIG. 9.

FIG. 11 is a perspective view of a first alternative embodiment of a dilation restrictor member usable in conjunction with the exovascular stent device of the present invention.

FIG. 12 is a perspective view of a second alternative embodiment of a dilation restrictor member usable in conjunction with the exovascular stent device of the present invention.

FIG. 13 is a perspective view of a first alternative embodiment of an exovascular stent device of the present invention.

FIG. 14 is a perspective view of a second alternative embodiment of an exovascular stent device of the present invention.

FIG. 15 is a perspective view of a modified single-piece embodiment of a vascular implant system of the present invention incorporating (a) an exovascular stent device component and (b) two (2) dilation restrictor member components.

FIG. 16 is a longitudinal sectional view through line 16—16 of FIG. 15.

FIG. 20a is a perspective view of a segment of bioprosthetic blood vessel having a venous valve positioned therein.

FIG. 20b is a perspective view of an endovascular stent device of the present invention.

FIG. 20c is a perspective view of the endovascular stent device of FIG. 20b positioned on and sutured to the bioprosthetic graft segment of FIG. 20a.

FIG. 20d is a longitudinal section view through line 20d—20d of FIG. 20b.

FIGS. 21a–21f is a step-by-step schematic diagram illustrating a method of implanting a bioprosthetic venous valve within an in situ blood vessel utilizing an endovascular stent device of the present invention.

DETAILED DESCRIPTIONS OF PREFERRED EMBODIMENTS

Figure 17:
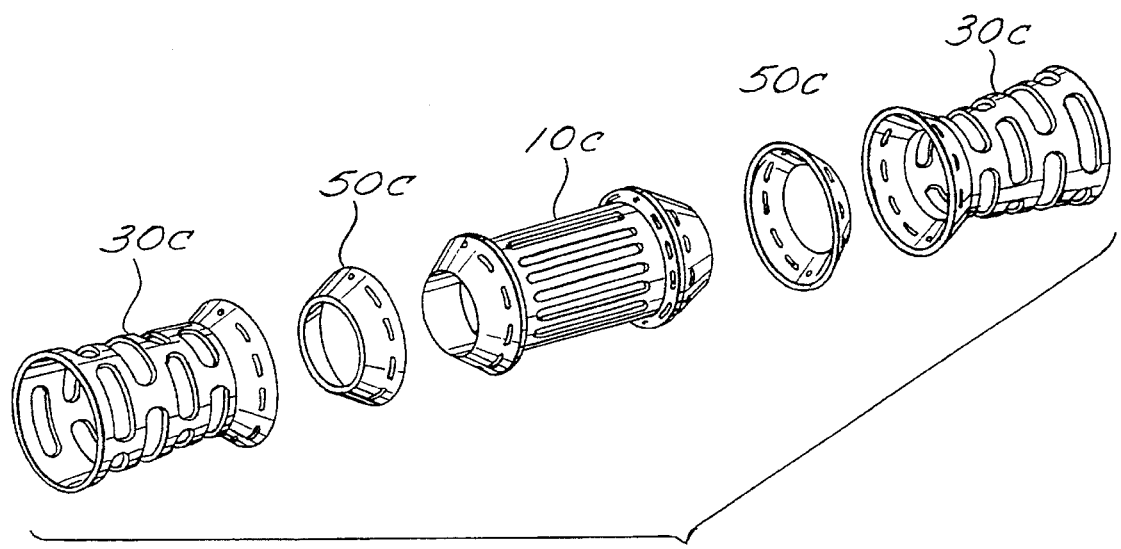
FIG. 17 is an exploded perspective view of a modified version of the vascular implant system shown in FIG. 15, said modified version having tapered interfacing surfaces on adjacent components to facilitate alignment of the components.

The following detailed descriptions and the accompanying drawings are provided for the purpose of illustrating and describing certain presently preferred embodiments of the invention. The following detailed descriptions and drawings are not intended to limit the scope of the invention in any way.

i. Exovascular Blood Vessel Stent Device

In accordance with the invention there is provided an exovascular blood vessel stent device 10 which is useable to form a tubular implant prosthesis 13. The exovascular stent device 10 of the present invention serves to hold and support a segment of tubular graft material such as a segment of blood vessel. In particular, the exovascular stent device 10 of the present invention may be utilized in conjunction with a preserved segment of vein having a venous valve position therein. In such embodiment, the exovascular stent device 10 coupled with the preserved section of venous valve having the venous valve located therein results in the formation of a venous valve implant prosthesis.

One embodiment of an exovascular stent device 10 of the present invention is shown in FIGS. 1–5. Referring to FIGS. 1–5, the stent device 10 comprises a cylindrical body having a hollow inner bore 22 extending longitudinally therethrough and having a plurality of fluid passage apertures 18, such as elongate slots (FIG. 2), formed therein.

A first end flange 14 is formed on one end of the cylindrical stent body and a second end flange 16 is formed on the opposite end of the cylindrical stent body. Suture holes or apertures 20 are formed in end flanges 14, 16 to facilitate suturing of a bioprosthetic blood vessel segment 12 to the exovascular stent 10.

Initially, a segment of blood vessel 12, such as a segment of vein 12 having a venous valve (V) formed therein, is excised and removed from a cadaverous human or animal source. Excess tissue is removed from the segment of blood vessel 12 and the prepared segment of blood vessel 12 is thereafter immersed in or otherwise exposed to one or more chemical fixative or preservative solutions for a period of time sufficient to chemically fix or tan the collagenous matrix of the blood vessel segment 12, thereby forming a preserved bioprosthetic vascular graft.

Typically, the vein segment 10 is immersed in a chemical fixative solution known to cross-link collagen molecules for purposes of chemically "fixing" the collagenous network of the bioprosthetic vein graft. Examples of such chemical fixative solutions include formaldehyde, glutaraldehyde, dialdehyde starch, hexamethylene diisocyanate and certain polyepoxy compounds including glycol diglycidyl ether, polyol polyglycidyl ether, and dicarboxylic acid diglycidylester.

After the chemical fixation process has been completed, the "fixed" segment of blood vessel is inserted into the hollow bore 22 of the exovascular stent device 10 such that some portion of the vein segment 12 extends out of and protrudes beyond the opposite ends of the stent device 10. The protruding ends of the prosthetic vein segment 12 are then rolled back or splayed laterally such that they abut against the outer faces of the lateral end flanges 14, 16. Portions of the vein segment 12 which extend outboard of the outer edge of the flanges 14, 16 are then trimmed or cut away such that the ends of the vein segment 12 are substantially flush and even with the outer edges 24, 26 of the flanges 14, 16.

Sutures 28 are then passed through the ends of the vein segment 12 and through the suture apertures 20, thereby suturing the vein segment 12 to the exovascular stent device 10 to form a substantially unitary implant prosthesis which comprises 1.) the vein segment 12 and the surrounding stent 10. It is preferable that the suture apertures 20 be slightly elongate as shown, and sufficiently large to permit easy passage of a standard suture needle and suture material (e.g. 4-0 nylon) therethrough.

At the time of surgical implantation, the implant unit may be used in conjunction with one or two dilation restrictor members 30. Alternatively, the implant unit may be used with one or two anastomosis rims 31.

ii. Dilation Restrictor Members

In accordance with the invention, there is provided a dilation restrictor member which functions to restrict the degree to which a blood vessel may dilate in a region immediately adjacent an existing suture line. The dilation restrictor member 30 of the present invention may be utilized as an independent device or, alternatively, may be utilized in conjunction with the above-described exovascular stent device to form a complete vascular implant system.

The dilation restrictor member 30 comprises a generally cylindrical body having a flange member 32 formed on one end thereof. The cylindrical body of the dilation restrictor member 30 may be tapered such that the diameter of such cylindrical body is smaller at the end adjacent the flange 32 than at the opposite end thereof. An example of such tapered configuration of the dilation restrictor member 30 is shown in FIG. 6. In such tapered embodiment, it is desirable generally cylindrical or frusto-conical section of the restriction member 30 be configured such that its diameter gradually increases, thereby providing a gradual taper against which the outter surface of the blood vessel may abut when the blood vessel undergoes dilation or diametric enlargement.

The dilation restrictor member 30 serves two (2) functions. First, it operates as an appliance to (a) facilitate suturing of the implant prosthesis 13 into the desired blood vessel. Second, the dilation restrictor member operates to restrict dilation of the blood vessel 40 at regions immediately adjacent the points of anastomosis to the vascular implant prosthesis 13. By restricting or limiting the dilation of the blood vessel 40 at regions immediately adjacent the implant prosthesis 13, the dilation restrictor members 30 function to prevent or minimize variations in internal blood vessel diameter between the inner diameter of the implant prosthesis 13 and the inner diameter of the adjacent blood vessel 40. Such limitation helps to ensure laminar or non-turbulent flow of blood through the blood vessel 40 and implant prosthesis 13 without excessive turbulence.

In operation, the dilation restrictor member 30 is passed over the cut end of the blood vessel 40 such that the cut end of the blood vessel 40 protrudes slightly beyond the opening of the inner bore 23 of the dilation restrictor member 30 at the flange 32 end thereof. The end of the blood vessel 40 is then splayed outwardly such that the outer surface of the blood vessel 40 abut against the outboard face of the flange 32. The end of the blood vessel 40 is then cut or trimmed such that on dilation of the blood vessel 40 immediately adjacent the points of anastomosis to the implant prosthesis terminates flush with or substantially even with the outer periphery 42 of the flange 32. Sutures 44 are then passed through the end of the blood vessel 40 and the suture apertures 34 to secure the end of the blood vessel 40 to the flange 32.

The exposed luminal surface of blood vessel 40 which faces away from the outboard face of the flange 32 may then be placed in direct abutment with the exposed luminal surface of the prosthetic vein segment 12 which faces away from the outboard surface of adjacent lateral end flange 14 or 16 of the supporting stent device 10. A series of interrupted or noninterrupted sutures 50 may then be passed through the apertures 20, 34 and the interpositioned tissue of the blood vessel 40 and prosthetic vascular segment 12 to effect anastomosis of the prosthetic implant 13 to the blood vessel 40.

iii. Optional Spacer Rings

An optional spacer ring or washer 50 may be interposed between the tissue of the blood vessel 40 and the tissue of the prosthetic vascular graft 12 to prevent the living blood vessel tissue 40 from coming in direct contact with the preserved tissue of the prosthetic vascular graft 12. The use of such spacer ring or washer 50 may minimize or prevent immunological reactions within the adjacent blood vessel 40 due to contact with the preserved tissue of the prosthetic vascular graft 12.

Such optional spacer ring or washer 50 may comprise a flat disc formed of biocompatible plastic such as Delrin™, acetyl resin (Dupont, Wilmington, Del. 19898), Teflon™, or other suitable materials. The central aperture 52 of the spacer ring or washer 50 is preferably of the same inner diameter D as that of the flange end opening of the dilation restrictor member 30, and that of the end openings of the cylindrical bore 22 of the exovascular stent member 10. Such size matching of the inner diameters D of the adjacent portions of a.) the exovascular stent member 10, b.) the spacer ring washer 50, and c.) the central bore 23 of the dilation restrictor member 30 will prevent or minimize the likelihood of excessive turbulence or nonlaminar flow within the blood vessel due to excessive variations of inner diameter of the blood vessel, as may result if the implant components are not size matched.

iv. Vascular Implant System and Method of Use

Figure 18:
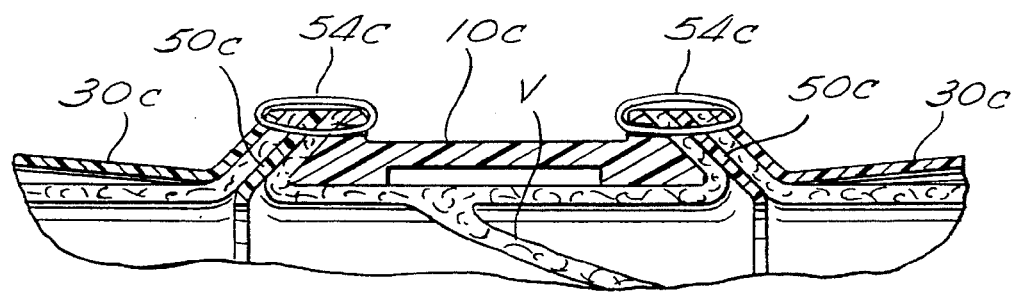
FIG. 18 is a longitudinal sectional view of the vascular implant system shown in FIG. 17 when operatively positioned and mounted on an in situ blood vessel.
Figure 19A:
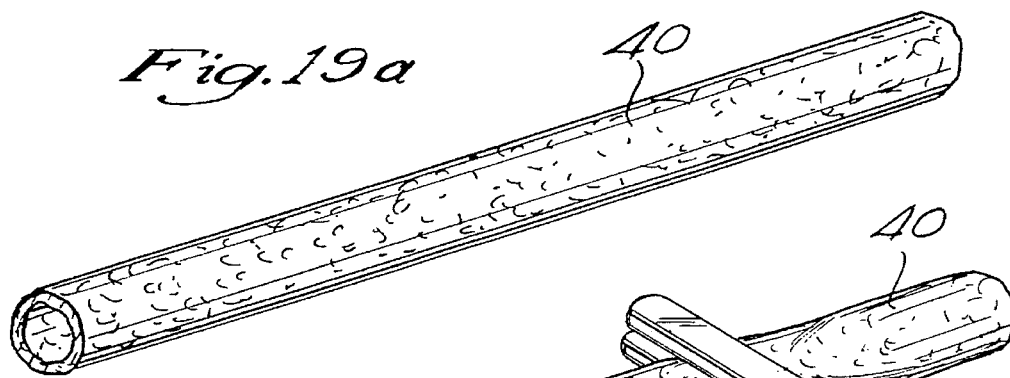
FIGS. 19a–19d are step-by-step schematic diagrams illustrating a method of implanting a prosthetic vascular graft utilizing a vascular implant system of the present invention.
Figure 19B:
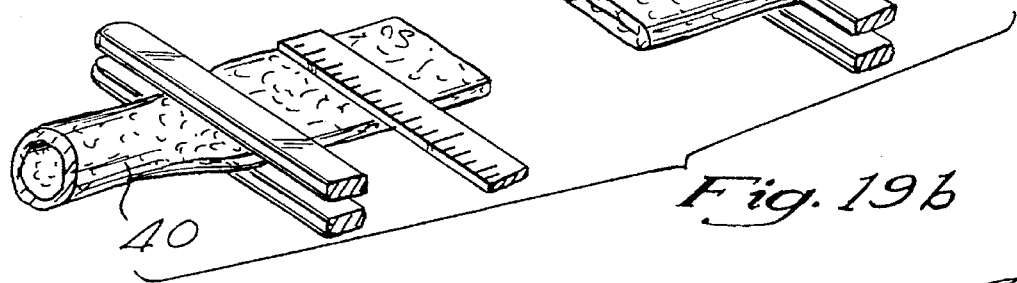
Figure 19C:
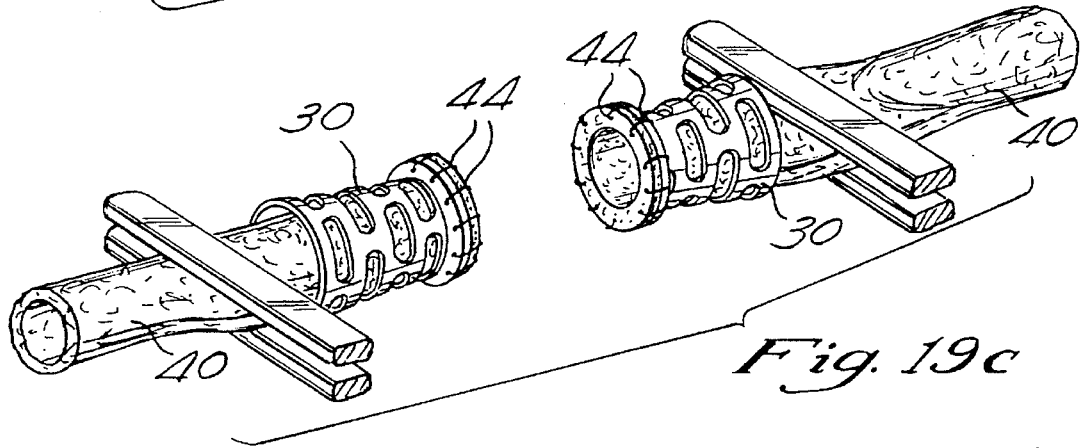
Figure 19D:
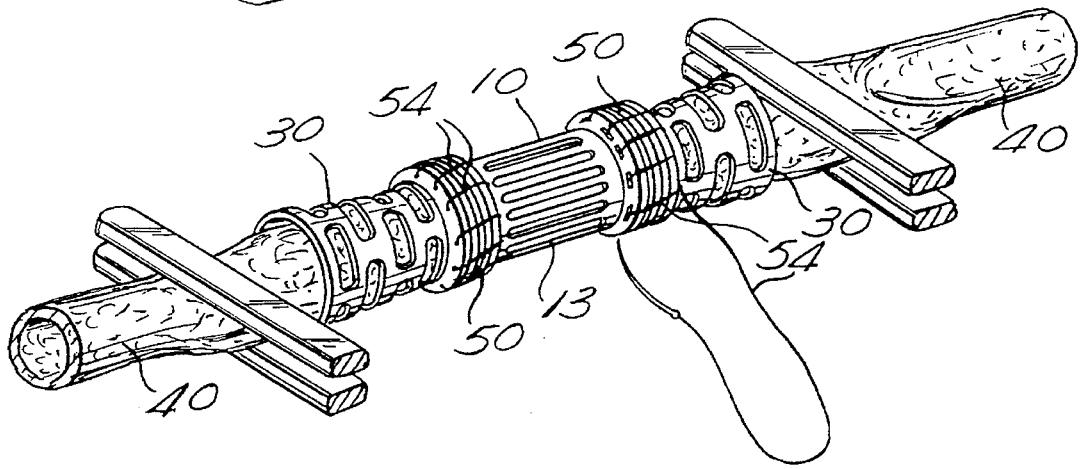

The exovascular 10 the present invention may be coupled with one or more dilation restrictor members 30 to form a vascular implant system. Optionally, such vascular implant system may further incorporate spacer rings or washers 50. The individual exovascular stent 10, dilation restrictor member(s) 30 and optional spacer ring(s) or washer(s) 50 may be independently formed as separate components as shown in FIGS. 9, 10, 17 and 18 or, alternatively, may be formed as a single-piece system as shown in FIGS. 15 and 16.

In embodiments of the invention wherein the exovascular stent 10 dilation restrictor member (s) 30 and optional spacer ring(s) or washer(s) 50 are favored as separate components the dilation restrictor members 30 are positioned on the opposing cut ends of blood vessel 40 with each cut end of blood vessel 40 being splayed outwardly and affixed to the outer face of the dilation restrictor member flange. The bioprosthetic implant unit 13 incorporating the exovascular stent 10 is positioned therebetween. Spacer rings or washers 50 may be interposed between the opposing surfaces of the blood vessel 40 and the prosthetic vein segment 12 so as to prevent direct tissue-to-tissue contact therebetween. Full thickness sutures are then utilized to anastomose the components in end-to-end abutting relation, as shown in FIGS. 9 and 10. Notably, the sutures 54 pass through the flanges 14 or 16 and 32, through the adjacent out-turned tissue of the blood vessel and/or vascular implant 12 and through the optional washer or spacer 50. Such sutures 54 thus remain outside of the blood-transporting vessel lumen and do not come in contact with the flow of blood which normally passes through the vessel following the implant surgery.

v. Anastomosis Rings

In applications where it is not desired to utilize a dilation restrictor member 30, a simple anastomosis ring 31, as shown in FIG. 12, may be employed. Such anastomosis ring 31 comprises a rigid cylindrical rim 37 having a perpendicular flange 33 formed on one end thereof. suture apertures 35 are formed through the flange 33 as shown.

In operation, the rim 37 of the anastomosis ring 31 is passed over the outer surface of the cut end of blood vessel 40. The cut end of blood vessel is then splayed outwardly or rolled back such that the outer surface of the blood vessel abuts against the outboard surface of flange 33. The end of the blood vessel 40 is then cut or trimmed so as to terminate substantially flush with the outer periphery of flange 33.

Interrupted or uninterrupted sutures are passed through suture apertures 35 and the adjacent tissue of the blood vessel 40 to affix the anastomosis ring 31 to the cut end of the blood vessel 40 in the desired manner.

Thereafter, the luminal surface of the blood vessel 40 which faces away from the outboard surface of the flange 33 of anastomosis ring may be placed in direct abutment with the surface of prosthetic vein segment 12 which faces away from the outboard surface of the flange number 16 of the exovascular stent 10. Optionally, a spacer ring or washer 50 may be interposed between the opposing surfaces of the blood vessel 40 and the prosthetic vein segment 12, as described above with respect to the dilation restrictor member embodiment of the invention.

Interrupted or uninterrupted sutures 50 are then passed through the adjacent tissues of the blood vessel 40 and prosthetic vein segment 12, through the adjacent suture apertures 20 and 35 of the stent device 10 and anastomosis ring 31, respectively, and through any optionally interposed spacer ring or washer 50 so as to effect anastomotic coupling of the prosthetic implant 13 to the blood vessel 40.

In embodiments of the invention wherein the exovascular stent 10, dilation restrictor member(s) 30 and optional spacer ring(s) or washer(s) 50 are formed as a single piece system (80 FIGS. 15 and 16). The exovascular stent component 10 will comprise the mid-portion 82 of such single-piece system and will be formed of relatively rigid material such as acetyl resin (Delrin™, Dupont, Wilmington, Del. 19898). The lateral end portions 84 of such single-piece system 80 comprise the dilation restrictor member(s) 30 and are formed of elastomeric material having greater elasticity than the relatively rigid mid-portion 82 of the single-piece system 80. Suture apertures 81 may be on the flange members 16*b* of the mid-portion 82 of the single-piece system 80 to permit passage of sutures 50A through the relatively rigid material of the mid-portion 82 of the system 80. On the otherhand, if the elastomeric material of the lateral end portions 84 of the single-piece system 80 is sufficiently flexible to be punctured by a suture needle, there need be no pre-cut suture apertures formed in the flange portion 32*b* of such relatively flexible lateral end portions 84 of the system 80.

Initially, a preserved segment of blood vessel 12*b* is positioned within the mid-region 82 of the single-piece system 80 such that the ends of the preserved segment of blood vessel 12*b* are splayed outwardly and positioned adjacent the end flanges 14*b*, 16*b*. The ends of the blood vessel segment 12*b* are affixed to the outboard surfaces of the end flanges 14*b*, 16*b* by way of an appropriate adhesive or by individual sutures 86. In embodiments where individual sutures 86 are employed, an additional set of suture passage apertures 26*b* may be formed in the end flanges 18*b*, 14*b* to accommodate passage of such sutures 86.

With the prosthetic segment of blood vessel 12*d* affixed within the mid-portion 82 of the single-pieced system 80, the entire system 80 may be sterilized and stored in an appropriate storage solution such as glutaraldehyde or dilute ethanol.

At the time of implantation, the system 80 having the prosthetic segment of blood vessel 24*b* mounted therein is rinsed and prepared for implantation. A section of blood vessel 40*b* is excised and removed. The removed section of blood vessel corresponds to the length L of the mid-region 82 of the single-piece system 80.

vi. Endovascular Venous Valve Stent Device

Further, and in accordance with the invention, there is provided an endovascular stent device 100 which is useable to form an endovascular venous valve bioprosthesis 120. Such venous valve bioprosthesis is implantable inside the lumen of a vein through an incision formed on the wall of the vein.

One embodiment of the endovascular venous valve stent device 100 of the present invention is shown in FIG. 20*b*. Such endovascular venous valve stent device 100 is formed of rigid, bio-compatible materials such as nylon, or Delrin™ (acetyl resin; Dupont, Wilmington, Del. 19898). Such endovascular stent 100 comprises a generally cylindrical or tubular body having a hollow bore 108 extending longitudinally therethrough. The inflow end of the rigid body 102 comprises a straight cut frustrum establishing a generally flat, round opening into the hollow inner bore 108 of the rigid body 102. The outflow end of the rigid body 102 comprises two apical support struts 104, 106. Such apical support struts 104, 106 are positioned on opposite sides of the rigid body 102 such that a fixed segment of blood vessel having a venous valve therein may be positioned between and affixed to said support struts 104, 106, with the lateral edges of the leaflets of the venous valve positioned therein being directly adjacent to said lateral support struts 104, 106, such that the leaflets of the venous valve will traverse between the laterally positioned support struts 104, 106 in the manner shown in FIG. 20*c*.

Suture apertures 110 are formed at various locations on the rigid body 102 to permit affixation of a segment of blood vessel 118 to the endovascular stent 100 by way of sutures.

At least one annular groove or ridge is formed around the rigid body 102 to receive or facilitate seating of a ligature therein such that the implant must be held in place by way of one or more blood vessel surrounding ligatures 152, as shown in FIG. 21*f*.

vii. Preparation of a Venous Valve Bioprosthesis for Endovascular Implantation A preserved segment of vein 118 having a venous valve 119 positioned therein may be mounted within the endovascular stent device 10 of the present invention to form an endovascular venous valve prosthesis 120, as shown in FIG. 20*c*.

Prior to preparation of the endovascular venous valve prosthesis 120, a segment of vein 118 having a venous valve 119 positioned therein is harvested from an autologous or homologous source and is subjected to any desired preparation, chemical fixing or other preservation steps such as those described in relation to the prosthetic implant 13 described hereabove.

After the segment of vein 118 has been fully fixed and preserved, it is coaxially inserted through the hollow bore 108 of the endovascular stent 100, such that the opposite ends of the segment of vein 118 will extend out of and beyond the inflow and outflow ends of the endovascular stent device 100, as shown in FIG. 20*c*. The segment of vein 118 is rotated and positioned such that the leaflets 122, 124 of venous valve 119 extends transversely between the opposing support struts 104, 106 of the endovascular stent 110.

The portion of the vein segment 118 which extends out of and beyond the inflow end of the endovascular stent 100 is rolled back over the inflow end of the stent 100, trimmed and affixed to the body 102 of the stent 100 by way of a series of interrupted or uninterrupted sutures 126.

Longitudinal incisions 128, 130 may be formed on opposite sides of the end portion of the vein segment 118 which extends out of and beyond the outflow end of the stent 100. After incisions 128 and 130 have been formed, that portion of the vein segment 118 may be rolled back over the outer surface of the body 102 of stent 100, trimmed, and affixed to the stent by rows of appropriately placed sutures 132, 134. Thus, the vein segment 118 having venous valve 119 formed therein combines with the endovascular stent 100 to form an endovascular venous valve implant prosthesis 120.

A presently preferred method of surgically implanting the endovascular venous valve prosthesis 120 is illustrated in FIGS. 21*a*–*f*.

Initially, the blood vessel 140 into which the endovascular venous valve prosthesis 120 is to be implanted is cross-clamped at first 144 and second 146 locations, on either side of the location at which the implant is desired to reside. Thereafter, an incision 142 is formed in the blood vessel 140, between the cross-clamp locations 144, 146. The incision 142 is sufficiently large to permit the implant 120 to be inserted therethrough.

Double needle sutures 148, 150 are passed through the suture apertures 110 located at or near the tips of the support struts 104, 106 of the implant 120. Double needle sutures 148, 150 thus form convenient means for pulling or towing the implant 120 to a desired location within the lumen of the blood vessel 140, as illustrated in FIGS. 21c and 21d. Accordingly, the needles of sutures 148 and 150 are grasped by a needle holder instrument, inserted through incision 142 into the lumen of blood vessel 140 and subsequently passed outwardly through the wall of the blood vessel 140 at opposite locations whereat it is desired to have the outflow end of the implant 120 reside. Thereafter, the sutures 148 and 150 may be pulled in the direction of arrows A while the implant 120 is gently guided through the incision 142, as shown in FIG. 21d. The pulling of sutures 148, 150 in the direction of arrows A is continued until the implant 120 has been fully received within the lumen of the blood vessel 140 and advanced to its desired location of residence. Mild tugging pressure may be maintained on sutures 148, 150 to ensure that the implant 120 will remain in its desire residence location during subsequent closure of the incision 142 and until application of a permanent holding ligature 152.

The incision 142 may be closed by appropriate vascular sutures or any other known means for closing such incision. After the incision 142 has been closed, the holding ligature 152 is position around the outer circumference 140 and snuggly tied in place so as to be nested within the annular groove 112 of the stent 100. Such nesting of the ligature 152 within the annular groove 112 of the stent 100 serves to firmly hold the implant 120 at its desired location of residence.

After the holding ligature 152 has been applied, one or both of the needles on two needle sutures 148 and 150 may be cut off and the sutures 148 and 150 extracted and removed. Alternatively, the sutures 148 and 150 may be tied on the exterior surface of the blood vessel 140 and remain in place to provide additional holding of the implant 120 at its desired location of residence.

Although the invention has been described herein with reference to specific embodiments thereof, it will be appreciated that various alterations, additions, or modifications may be made to the herein described embodiments without departing from the intended spirit and scope of the invention. Accordingly, it is intended that all such alterations, additions and modifications be included within the scope of the following claims or the equivalents thereof.

What is claimed is:

1. A vascular implant prosthesis, comprising:
   a) an exovascular stent comprising:
      a generally elongate cylindrical body, a first end, a second end, and a hollow bore extending longitudinally therethrough;
      a first flange extending perpendicularly about the first end of the stent body;
      a second flange extending perpendicularly about the second end of the stent body;
      a plurality of apertures formed in the stent body to permit flow of fluid therethrough;
   b) a bioprosthetic vascular graft comprising a segment of mammalian blood vessel which has been treated with a chemical fixative known to cross link collagen, said bioprosthetic vascular graft being positioned coaxially within the bore of the stent body and affixed to the first and second end flanges of the stent.

2. The vascular implant prosthesis of claim 1 wherein the bioprosthetic vascular graft is affixed to the first and second end flanges by way of sutures.

3. The vascular implant prosthesis of claim 1 wherein said bioprosthetic vascular graft comprises a segment of vein.

4. The vascular implant prosthesis of claim 3 wherein a venous valve is formed within the segment of vein.

5. The vascular implant prosthesis of claim 4 wherein the venous valve was disposed in an open position when the vascular graft was treated with said chemical fixative.

6. The vascular implant of claim 4 wherein the venous valve was disposed in a closed position when the vascular graft was treated with said chemical fixative.

7. The vascular implant prosthesis of claim 1 wherein the tubular vascular graft comprises a segment of artery.

8. The vascular implant prosthesis of claim 1 wherein the apertures comprise a plurality of elongate slots formed around the cylindrical body of the stent.

* * * * *